United States Patent
Kline et al.

(10) Patent No.: US 11,375,974 B2
(45) Date of Patent: Jul. 5, 2022

(54) QUALITY CONTROL PROTOCOLS AND METHODS FOR DETERMINING REPLACEMENT AND PROPER LOCATION FOR LISTENING TO BODY FLUIDS

(71) Applicant: CVR Global, Inc., Denver, NC (US)

(72) Inventors: Bret Kline, Columbus, OH (US); Peter Bakema, Denver, NC (US); Young Truong, Carrboro, NC (US); Richard Finlayson, Greenville, NC (US); Orville Day, Greenville, NC (US)

(73) Assignee: CVR Global, Inc., Denver, NC (US)

( * ) Notice: Subject to any disclaimer, the term of this patent is extended or adjusted under 35 U.S.C. 154(b) by 554 days.

(21) Appl. No.: 16/309,803

(22) PCT Filed: Jun. 15, 2017

(86) PCT No.: PCT/US2017/037662
§ 371 (c)(1),
(2) Date: Dec. 13, 2018

(87) PCT Pub. No.: WO2017/218766
PCT Pub. Date: Dec. 21, 2017

(65) Prior Publication Data
US 2019/0142360 A1  May 16, 2019

Related U.S. Application Data

(60) Provisional application No. 62/350,268, filed on Jun. 15, 2016.

(51) Int. Cl.
*A61B 7/00* (2006.01)
*A61B 5/00* (2006.01)

(52) U.S. Cl.
CPC ............. *A61B 7/00* (2013.01); *A61B 5/6822* (2013.01); *A61B 5/6886* (2013.01);
(Continued)

(58) Field of Classification Search
CPC ....... A61B 7/00; A61B 5/7221; A61B 5/6886; A61B 5/6822; A61B 5/7405; A61B 5/742;
(Continued)

(56) References Cited

U.S. PATENT DOCUMENTS

| 6,671,643 B2 * | 12/2003 | Kaehler | ................. H04R 25/30 381/61 |
| 8,160,669 B2 | 4/2012 | Brauker et al. | |

(Continued)

*Primary Examiner* — Sean P Dougherty
*Assistant Examiner* — Alexander H Connor
(74) *Attorney, Agent, or Firm* — Vos-IP, LLC

(57) ABSTRACT

A method for determining proper placement of a sensor pod on a patient comprising: performing a first quality control procedure on a detection device, wherein said detection device comprises a base unit, at least two sensor pods, a computer system implementing appropriate software, and a display; wherein the first quality control procedure generates a tone from a speaker embedded within said base unit and wherein each of said sensor pods measures and compares the measured sound to a predetermined measurement in real-time; wherein a sensor pod is determined to have met quality control if said sound is within 10% of the predicted measurements; performing a second quality control procedure on said sensor pods, wherein said sensor pods measure sounds on a patient; wherein the system, once engage, detects sounds from the sensor pods and compares the detected sounds in real-time to a predicted sound based on the fluid flow vessel; and wherein said method provides for an audio or visual alarm when said sensor pod is not detecting the predicted sounds, indicating an improper location for the sensor pod.

12 Claims, 11 Drawing Sheets

(52) U.S. Cl.
CPC ............ *A61B 5/7221* (2013.01); *A61B 5/742* (2013.01); *A61B 5/7405* (2013.01); *A61B 2562/0204* (2013.01); *A61B 2562/046* (2013.01)

(58) Field of Classification Search
CPC ........ A61B 5/02007; A61B 2560/0276; A61B 2560/0223; A61B 2562/0204; A61B 2562/046
See application file for complete search history.

(56) References Cited

U.S. PATENT DOCUMENTS

| | | |
|---|---|---|
| 9,101,274 B2 | 8/2015 | Bakema et al. |
| 9,615,794 B2 | 4/2017 | Kaskoun et al. |
| 2002/0072684 A1 | 6/2002 | Stearns |
| 2005/0123146 A1* | 6/2005 | Voix ................. H04R 29/00 381/60 |
| 2008/0214949 A1* | 9/2008 | Stivoric ............. G01K 1/024 600/549 |
| 2011/0130675 A1* | 6/2011 | Bibian ............. A61B 5/6843 600/544 |
| 2012/0232427 A1* | 9/2012 | Bakema ............. A61B 7/04 600/586 |
| 2014/0081175 A1 | 3/2014 | Telfort |
| 2015/0051473 A1* | 2/2015 | Huang ............. A61B 5/0095 600/407 |
| 2015/0150505 A1* | 6/2015 | Kaskoun ........... A61B 5/6833 600/300 |
| 2015/0164387 A1* | 6/2015 | Varsavsky ........... G01N 27/026 702/182 |

* cited by examiner

QUALITY CONTROL PROTOCOLS AND METHODS FOR DETERMINING REPLACEMENT AND PROPER LOCATION FOR LISTENING TO BODY FLUIDS

CROSS-REFERENCE TO RELATED APPLICATION

This application is a 371 of PCT Application No. PCT/US2017/037662, filed Jun. 15, 2017, which claims the benefit of U.S. Provisional Application Ser. No. 62/350,268, filed Jun. 15, 2016, the disclosure content of which is hereby incorporated by reference in its entirety.

FIELD OF INVENTION

The present application is generally related to a method for performing quality control procedures, including determination of proper function of listening devices, and determination and guidance for determining the appropriate placement of an acoustic device on a body through signaling mechanisms used in connection with a mechanism that is detecting acoustic signals from the body.

BACKGROUND OF THE INVENTION

Detection of stenosis in the arterial circulatory system remains a challenge in the medical industry. Indeed, stroke and heart disease remain as two of the most likely cause of death among Americans each year. Existing technologies to detect stenosis or blockages remain in antiquated technologies, with few nascent technologies yet in the field. However, these tools can become critical in evaluation of patients for possible heart attack, stroke, and other injuries related to blockage of the cardiovascular system.

Infrasonic acoustic signals generated by a living organism can be useful in the detection and diagnosis of certain conditions or ailments of the organism. In particular, blood flow ire the organism cause infrasonic acoustic signals (e.g., via vibration of the arterial or venal walls) that indicate possible extent of stenosis, occlusion or aneurysm in the organisms' arteries and/or veins.

Certain prior patents, including U.S. Pat. Nos. 7,621,875 and 5,853,005 describe certain strategies for sensing acoustic signals in an organism. However, devices using these technologies were never commercialized due to numerous issues, including but not limited to the inability to actually identify relevant sounds within the arterial system. New devices, methods, and strategies for detecting acoustic sounds in the arterial circulatory system are needed to fill this gap in the medical industry.

SUMMARY OF THE INVENTION

The embodiments herein describe devices, systems, and methods for performing quality control procedures to a sensory device. Quality control procedures can be a self-diagnostic test or an active diagnostic test. Each quality control procedures is itself sufficient to ensure proper functioning of the device, however the two procedures can be seamlessly combined to ensure proper functioning of the device and proper positioning on a patient.

A first embodiments is directed towards a sensor base, comprising a charging component, a speaker, a processor, at least one sensor, and an indicator; wherein the charging component charges a sensor pod or sensor array placed on said sensor base, and the speaker is engaged to the processor, wherein the processor generates, and plays through the speaker, a predetermined sweep of sounds across the frequency and amplitude of sounds to be detected. A sensor placed on said sensor base detects the predetermined sweep of sounds and the indicator, confirms whether the sounds detected by the sensor are within a specified tolerance of the predetermined sweep of sounds. The indicator providing one signal to indicate within the tolerance, and a second signal to indicate failure of the tolerance, thus requiring replacement of the sensor. This ensures that the piezoelectric element is functioning properly in the range to be detected by the device for analysis. In certain embodiments, the sounds played are between 1-5000 Hz, which define a predetermined sound signature.

Where the sensor passes the test, the sensor is ready for use. If the sensor fails the test, the sensor or the base alerts the user to replace the sensor pod or disposable piezo assembly.

A further embodiment is directed towards a method of performing a self-diagnostic test on a sensor, comprising a base having a speaker and a processing unit, at least one sensor, comprising a piezoelectric unit, and at least one indicator, comprising: playing a predetermined sound signature from said speaker; detecting said sound signature with said sensor; processing said detected sounds and comparing said detected sounds to said predetermined sounds; indicating a failed sensor if the detected sounds are more than 25% apart from the predetermined sounds in frequency and intensity; and indicating proper function if said detected sounds are within 25% of the frequency of the predetermined sounds, wherein the sensor is ready for use. Where the indication is a failed sensor, the sensor will need to be replaced and the self-diagnostic test re-run. In certain embodiments both frequency and intensity are with a tolerance, for example 25% of a predetermined sound and intensity.

In certain embodiments, an active diagnostic test can be run immediately after the self-diagnostic test is run, wherein the active diagnostic test is a method for determining proper function of a sensor comprising, placing a sensor on a patient; detecting sounds from a patient; comparing said detected sounds from said patient to a predetermined signature; wherein a sensor is indicated as working properly if the detected sounds are within 25% of frequency of the predetermined signature, and indicated to fail if outside of 25% of the frequency.

In certain embodiments, an active diagnostic test can be run immediately after the self-diagnostic test is run, wherein the active diagnostic test is a method for determining proper function of a sensor comprising, placing a sensor on a patient; detecting sounds from a patient; comparing said detected sounds from said patient to a predetermined signature; wherein a sensor is indicated as working properly if the detected sounds are within 25% of frequency and intensity of the predetermined signature, and indicated to fail if both frequency and intensity are outside of that range.

In certain embodiments, an active diagnostic test can be run immediately after the self-diagnostic test is run, wherein the active diagnostic test is a method for determining proper placement and function of a sensor comprising: placing a sensor on a patient; detecting sounds from a patient; comparing said detected sounds from said patient to a predetermined signature; wherein a sensor is indicated as working properly if the detected sounds are within 25% of frequency of the predetermined signature, and indicated to fail if outside of that range. Wherein said sensor comprises at least three indicators, a first indicator signifying working properly, a second indicator signifying failure, and a third indicator signifying improper position, wherein an improper position indicator is generated where the frequency is between 25-50% off of the predetermined signature, wherein the sensor is re-positioned until a first indicator is signified. In certain embodiments, if no first indicator is signified within 30 seconds, a failure ($2^{nd}$) indicator is generated. In certain embodiments, a first indicator is green, a second indicator is red, and a third indicator is yellow.

In certain embodiments, the sound signature for active diagnostic test on a patient is listening for the "heartbeat" like Doppler hearing the "lub, lub." This sound is easily recognizable, and so the sound can be detected and transmitted, amplified, and played through the base speaker to indicate to the patient and to the tech, that the system is working. Furthermore, as this is a sound that is so well recognized, it may allow patients to relax or be familiar with the sound, and allow completion of the test with minimal or reduced anxiety.

In further embodiments, the sound signature is looking for the sound of flow through a particular arterial system. For example, flow through the carotid includes at least one sound signature at between 60-260 Hz. If the device does not pick up that sound, then it is not on the carotid or the carotid is highly stenosed. Accordingly, when testing the carotid, this may be a suitable sound signature. Even when this is the signature being used, it may be appropriate to still play or indicate another sound, for example, the heart beat sound.

A further embodiment is directed to an active quality control process, the method comprises: placing a sensor on the body, detecting a sound, comparing the detected sound to a sound signature, if the detected sound is within a predetermined tolerance of the sound signature proceed to start the test; if the detected sound is between 25 and 50% different than the predetermined sound signature, reposition the sensor, if the detected sound is more than 50% different than the predetermined sound signature, restart the self-diagnostic test. In certain embodiments, only the frequency is detected and used to determine the sound signature, as patient variability and environment can induce large variability that may increase false readings. Accordingly, in each embodiment, both frequency and intensity can be utilized, or only frequency for determining a sound signature.

In certain embodiments, a third indicator can illuminate if the sensor needs to be repositioned, and after repositioning, if a change in sound is detected, another indicator will illuminate, either the first and third, signifying the position is better, or the second and third, indicating the position is worse. This assists with re-positioning the sensor to the proper location until a first indicator is solely illuminated.

A method for determining proper position of sensor pod on a patient comprising: Performing a first diagnostic test on a sensor pod wherein said first diagnostic test is performed using a detection system comprising a base unit having a cradle, at least two sensor pods, a display and at least one alarm mechanism; wherein, while the sensor pods are engaged in the base unit cradle a base unit quality control procedure is performed to confirm that the sensor pods are properly functioning. After confirmation of the proper function of each of the sensor pods, the device is placed onto a patient wherein an active quality control procedure is performed. The active quality control program is run for between 5 and 30 seconds wherein each sensor pod is communicating with the computer of the system in real-time to ensure that each of the sensor pods is measuring the appropriate sounds. Wherein the system provides for an audio or visual notification that the quality control program is met, or wherein the system identifies one or more sensor pods that are improperly placed. Wherein the system then provides an alarm to any sensor pod that is not properly placed. Wherein a visual or audio mechanism is provided to provide real-time feedback as to the proper position for each sensor pod, and wherein one example provides for a red light for improper position and green light for a proper position.

A further embodiment is directed to a method above, wherein another audio or visual alarm or mechanism may be further included in the system so as to aid in the placement of the sensor pods on a patient.

A further embodiment is directed to an active quality control procedure wherein the sensor pod quality control step on the patient provides for immediate real-time feedback to the correct placement of each sensor pod to ensure fast and reliable positioning of the sensor pods, and also to confirm fast, precise, and accurate detection and determination of stenosis on the patient.

A method for determining proper placement of a sensor pod on a patient comprising: performing a first quality control procedure on a device, wherein said device comprises a base unit, at least two sensor pods, a computer system implementing appropriate software, and a display; wherein the first quality control procedure generates a tone from a speaker embedded within said base unit and wherein each of said sensor pods measures and compares the measured sound to a predetermined measurement in real-time; wherein a sensor pod is determined to have met quality control if said sound is within 5% of the predicted measurements; performing a second quality control procedure on said sensor pods, wherein said sensor pods measure sounds on a patient; wherein the system, once engaged, detects sounds from the sensor pods and compares the detected sounds in real-time to a predicted sound based on the fluid flow vessel; and wherein said method provides for an audio or visual alarm when said sensor pod is not detecting the predicted sounds, indicating an improper location for the sensor pod.

A further embodiment is directed to a method of confirming the proper position of a medical device upon a patient comprising: performing a first quality control procedure to ensure functioning of the sensor pods, comprising playing a predetermined set of sounds and comparing the predetermined sounds to the detected sounds; performing a second quality control procedure while detecting sounds from a patient wherein the test compares the detected sounds to sounds that are ordinarily present in detection of the particular artery or vessel of interest; and triggering an alarm wherein the detected sound does not meet the predicted sound, or triggering an approval if the detected sound confirms with the predicted sound.

A further embodiment is directed to a base unit that determines appropriate time for replacement of sensing devices, wherein said base unit comprises a computer implemented software connected to a database system, charging units, and a speaker, wherein the software plays a predetermined set of tones through the speaker and wherein a sensor pod placed within said base unit detects and displays the detected sound, which is compared to the predetermined set of tones played by the speaker; wherein replacement of a sensor pod is determined after the lesser of 50 quality control runs, or two quality control runs wherein the sensor pod diverges from the predicted sound by greater than 10%.

A further embodiment is directed towards a method of determining replacement of an acoustic sensing pod, comprising performing a quality control test of a base unit and at least one sensor pod, wherein said base unit comprises a computer implemented software connected to a database system, and a speaker, wherein a predetermined set of tones is played through the speaker and wherein a sensor pod placed within said base unit detects the detected sound, which is compared to the predetermined set of tones played by the speaker. The sensor pod is determined to be properly functioning wherein the detected sound differs from the pre-determined sound by less than 10% with regard to amplitude and frequency; and determined for replacement if outside of this tolerance. In certain embodiments, the sensor pod will automatically indicate replacement after a predetermined number of quality control runs. For example, at 25, 50, 75, or 100 runs will require or indicate replacement of the sensor pod.

A method for determining proper placement of a sensing pod on a patient comprising; placing a sensing pod on a patient adjacent to an area of interest; detecting sounds from the area of interest; comparing the detected sounds from the area of interest to a pre-determined sound signature; indicating proper placement if said comparison is within 25% of the detected sound as compared to the sound signature in frequency; indicating improper placement is said comparison if more than 25% variance between the detected sounds and the sound signature; moving said sensing pod on said patient until a proper placement is indicated. Generating a second indicator, providing indication if said placement is better or worse than a prior position relative to the % variance from the sound signature and detected sound.

A method for determining proper placement of a sensing pod on a patient comprising; placing a sensing pod on a patient adjacent to an area of interest; detecting sounds from the area of interest; comparing the detected sounds from the area of interest to a pre-determined sound signature; indicating proper placement if said comparison is within 25% of the detected sound as compared to the sound signature in both frequency and amplitude; indicating improper placement is said comparison is more than 25% variance between the detected sounds and the sound signature; moving said sensing pod on said patient and detected in a second sound and comparing said second sound to said pre-determined sound signature; and indicating replacement of said sensor pod wherein the variance is more than 75%.

A method for determining proper position of sensor pod on a patient comprising: performing a first diagnostic test on a sensor pod wherein said first diagnostic test is performed using an self-diagnostic test, comprising a base unit having a cradle for receiving said sensor pod, a speaker, a processing unit, a display, and at least one indicator; wherein while sensor pod is engaged in the base unit cradle and a predefined set of tones is played from the speaker and compared to the predefined set of tones for tolerance within 25% of the frequency of the predefined set of times; confirming proper function of each of the sensor pods within said 25% tolerance; placing said sensor pod onto a patient in a first position, wherein an active quality control procedure is performed; detecting sounds from the patient and comparing the detected sounds, in real-time, with an expected sound signature, wherein appropriate position is indicated when the detected sound is within 25% of the frequency of the expected sound; and wherein the system provides a second indicator if said detected sound is not within 25% of the frequency of the expected sound. The method further comprising moving the sensor pod to a second position if the sensor is not within 25% of the frequency of the expected sound. The method wherein another audio or visual alarm or mechanism may be further included in the system so as to aid in the placement of the sensor pods on a patient. The method wherein a set of indicators identifies whether the second position is closer to the 25% tolerance or farther away from said 25% tolerance from said first position. The method wherein the tolerance is 10%.

A method of confirming the proper position of a medical device upon a patient comprising: performing a first quality control procedure to ensure functioning of the sensor pods, comprising playing a predetermined set of sounds, detecting said predetermined set of sounds to create a first detected sounds, and comparing the predetermined sounds to the first detected sounds; performing a second quality control procedure by detecting a second detected sounds from a patient wherein the second quality control procedure compares the second detected sounds to a predetermined sound signature corresponding to the particular artery or vessel of interest; and triggering an alarm wherein the second detected sound does not meet the predetermined sound signature, or triggering an approval if the second detected sound is within a predefined tolerance from the predetermined sound signature. The method wherein the tolerance is 25%. The method of claim 6 wherein in the first setup, the comparison requires a tolerance of 25% to move to the second step.

A base unit for performing a self-diagnostic quality control process on at least one sensing pod; said base unit comprises a computer implemented software connected to a database system, charging units, and a speaker, wherein the software plays a predetermined set of tones through the speaker and wherein a sensor pod placed within said base unit detects and displays the detected sound, which is compared to the predetermined set of tones played by the speaker; wherein replacement of a sensor pod is determined after the lesser of 50 quality control runs, or two quality control runs wherein the sensor pod diverges from the predicted sound by greater than 10%.

A method of determining replacement of a wear unit comprising performing a quality control test of at least one sensor pod, comprising, placing said sensor pod onto a base unit, wherein said base unit comprises a computer implemented software connected to a database system, charging units, and a speaker, wherein the software plays a predetermined set of tones through the speaker and wherein a sensor pod placed within said base unit detects and displays the detected sound onto a display, which is compared to the predetermined set of tones played by the speaker; and determining whether to replace said sensor pod, wherein replacement of a sensor pod is determined after the lesser of 50 quality control runs, or two quality control runs wherein the sensor pod diverges from the predicted sound by greater than 10%.

A method for performing a quality control procedure on a listening device comprising: a listening device having at least one sensing element, and a base, said base comprising at least one speaker and a processing unit capable of playing a pre-determined set of tones through said speaker; playing a pre-determined set of tones through said speaker; detecting said pre-determined tones in said at least one sensing element; comparing the pre-determined tones to the detected tones; providing an indicator that the pre-determined tones are within a pre-determined tolerance of the detected tones and indicating an approval if the detected tones are within said tolerance and a rejection of the detected tones are outside of said tolerance; placing said sensing element on a patient adjacent to the carotid artery; detecting sounds from the carotid artery; comparing the sounds from the carotid artery to a predetermined carotid sound; providing a notification that the detected sounds from the carotid artery are within a pre-determined tolerance, or a rejection if the detected sounds are outside of the pre-determined tolerance; where the detected sounds are within the pre-determined tolerance, detecting sounds from the carotid artery and saving into storage for processing said sounds. The method wherein the indicator or the notification is selected from a tone, light, visual, or audio indication. The method wherein the indicator or notification is provided on the base unit, the sensor pod, the array, or combinations thereof. The method wherein the indicator and the notification are the same. The method wherein a further step comprises replacing said sensing element if a rejection is provided, and restarting the quality control procedure. The method wherein a further step comprises replacing said sensing element if a notification is provided, and restarting the quality control procedure.

A system for determining proper function and placement of a listening device; comprising a base unit comprising a speaker, computer implemented memory, and a processor, and a listening device comprising at least one sensing element; wherein said system generates a tone from said speaker and wherein said at least one sensing element detects said tone from said speaker and indicates to said processor whether the sensing element is detecting said tone within 25% of the actual frequency of the tone generated.

A method of performing a diagnostic test on a stenosis detection device; said stenosis detection device comprising at least one sensing element in electrical communication with a processor; and a base unit, in electrical communication with said processor; said base unit comprising a speaker and memory; playing a predetermined set of tones from said speaker; receiving said predetermined set of tones with said sensing element; processing in said processor said received tones and comparing said received tones to said predetermined set of tones; indicating success of said diagnostic test if said received tones are within 25% of the frequency of said predetermined set of tones; indicating failure of said diagnostic test if said received tones are more than 25% of the frequency of said predetermined set of tones, and replacing said sensing element and re-starting said quality control test; placing said stenosis detecting device onto a patient once a success is indicated; detecting sounds from said patient; comparing said detected tones to a predetermined fingerprint; and indicating success if said comparison is within 25% of said predetermined fingerprint with regard to frequency; and indicating failure if said comparison is outside of 25% of said predetermined fingerprint with regard to frequency; moving said sensing device on said patient until a success is indicated on said patient; and begin capturing data from said patient once success is indicated on said patient. The method wherein the sensing element is a piezo.

A method for performing a quality control process on a sensor comprising: placing a sensor adjacent a skin surface of a patient, said sensor comprising a piezoelectric element for detecting waves generated under said skin surface; detecting said waves with said sensor; comparing said detected waves to a predetermined sound fingerprint corresponding to the area of skin surface being tested; determining whether said piezoelectric element is functioning if said detected waves are within a predetermined tolerance of said sound fingerprint; replacing said piezoelectric element if said detected waves are outside of said tolerance; and proceed to take a data sample from said patient if said detected waves are within said predetermined tolerance.

DETAILED DESCRIPTION OF THE PREFERRED EMBODIMENTS

The present invention describes certain quality control methods or protocols that can be use in part in whole. The quality control protocols embodiments provide for a first process or method for determining if a listening device, such as a piezoelectric device, or microphone, is properly functioning. This is a self-diagnostic quality control feature. A second test is an active quality control procedure, which is med with sensors on a patient. The two tests can be used alone, each being sufficient to confirm that the sensor is working properly, or can be used together, to both ensure proper function and also proper placement of the sensors on a patient. When performed together, the tests are performed sequentially, first the self-diagnostic test and then the active, diagnostic test on the patient.

The devices of the present embodiment, and the methods used to confirm their correct function, are highly sensitive listening devices comprising a piezoelectric device capable of detecting a wide range of frequencies at low intensity. In essence, the piezoelectric device is a highly sensitive microphone and like any sensitive instrument, must be properly scrutinized and tested to ensure accuracy of the device and proper function.

The devices are intended for evaluation of blockage in the carotid arteries or other fluid flow vessels. In order to make determination of blockage, the device listens for certain signatures sent in the flow vessel. Accordingly, precise and proper functioning of the listening devices is required to ensure accurate determination of blockage in the fluid flow vessels. While these piezoelectric: devices are sufficient for use over at least several uses, the components can and do wear, or may be damaged by use.

Figure 1:
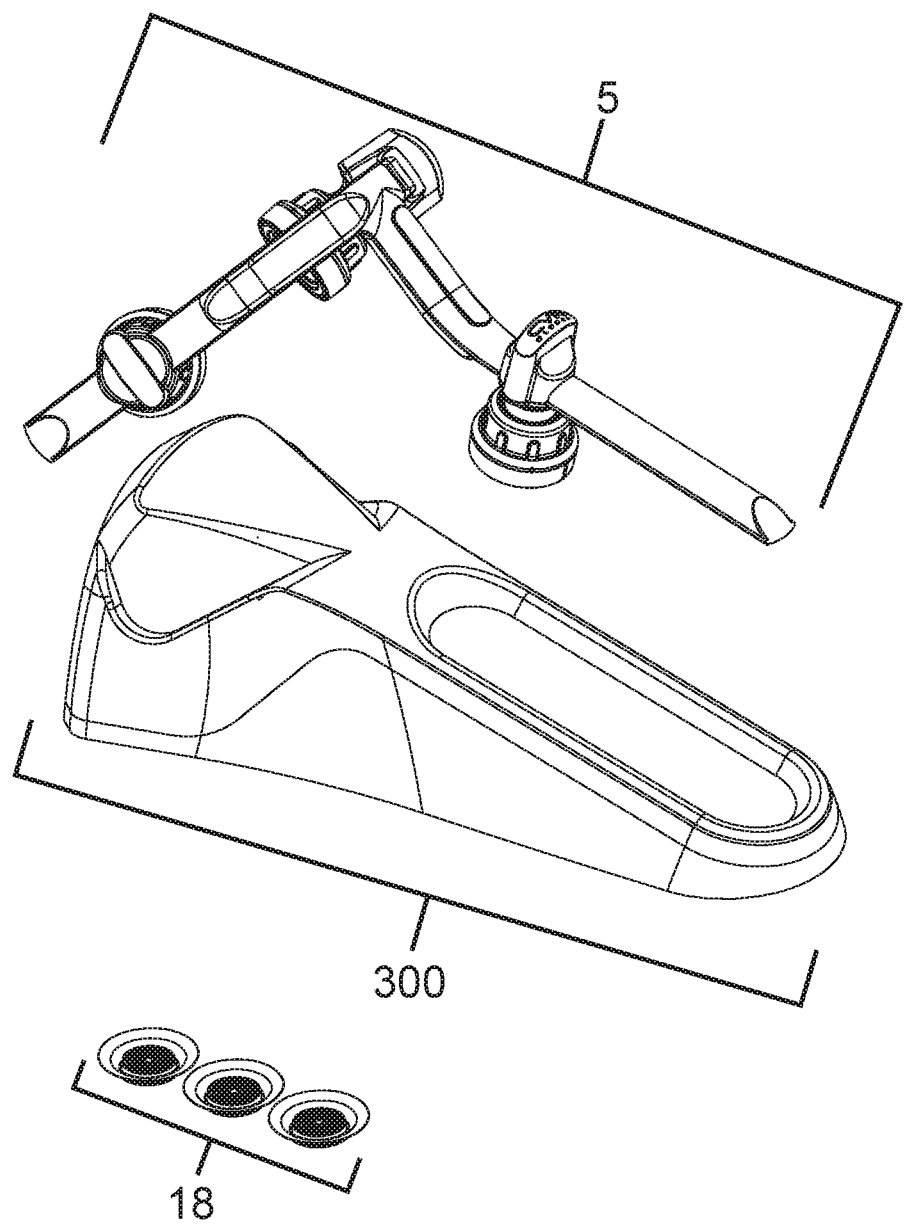
FIG. 1 depicts an array on a base.
Figure 4:
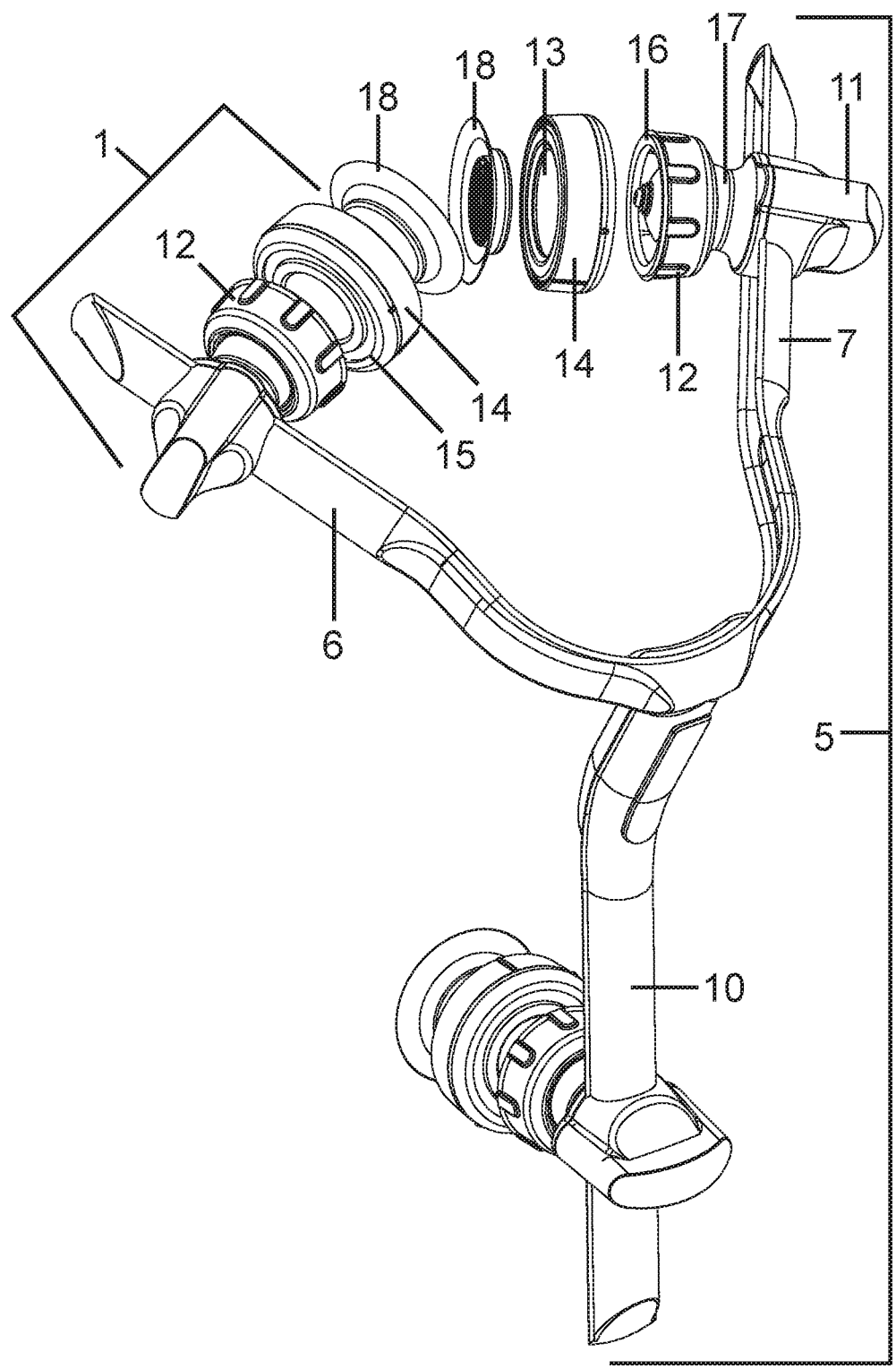
FIG. 4 depicts a detail of a partially exploded array, with replaceable components.
Figure 5:
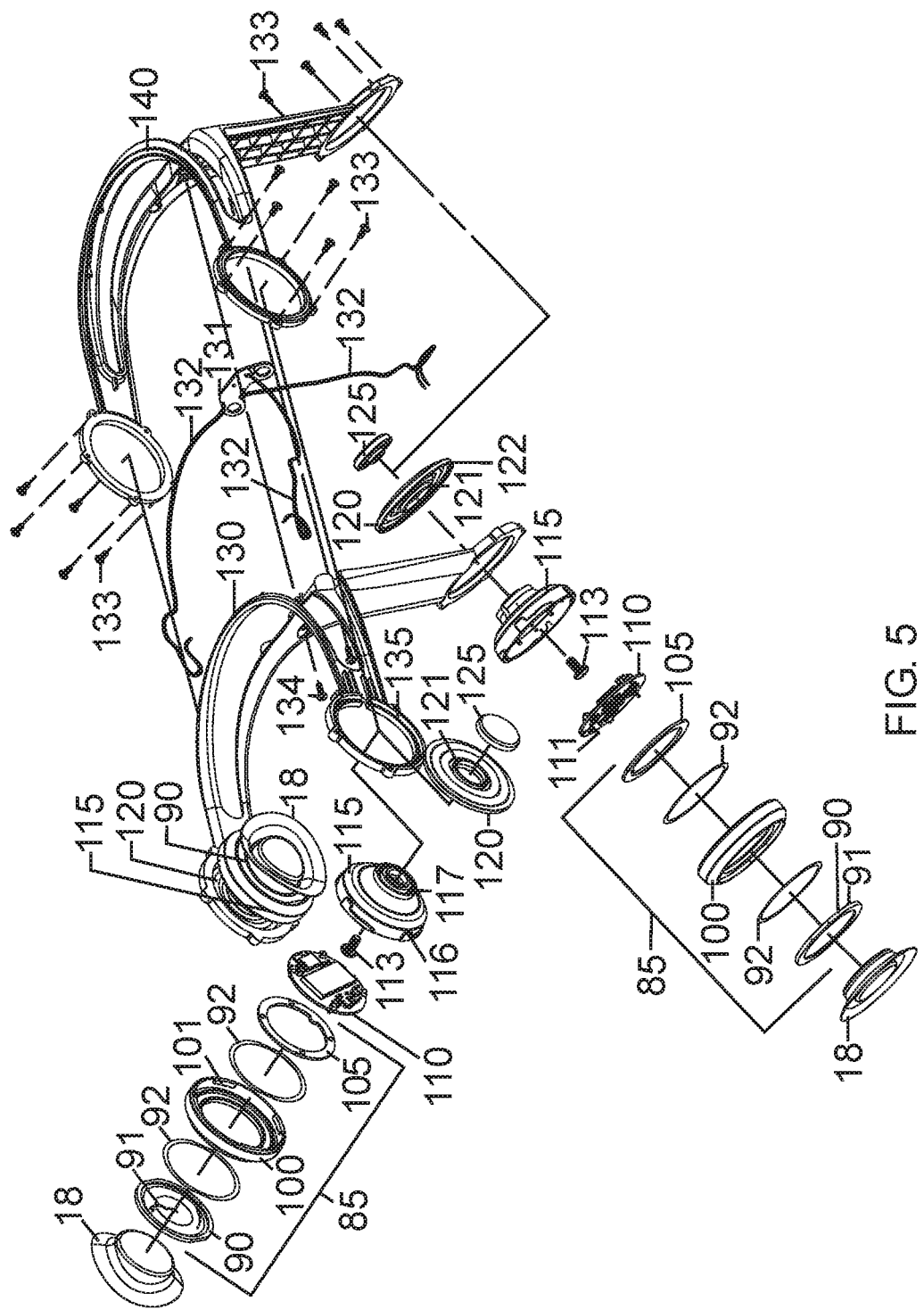
FIG. 5 depicts an exploded view of a further embodiment of an array and sensor pod.

Accordingly, in preferred embodiments, methods exist for determining the proper function of the sensitive piezoelectric components. FIG. 1 depicts a first embodiment comprising an array 5 positioned over a base 300. The array 5, is but one example of a configuration of, as pictured here, three listening pods. Embodiments of sensory pods, as depicted in greater detail in FIGS. 4 and 5 depict a sensor pod attached to an array. FIG. 5, in particular, depicts a piezo sensor 90, which is the primary component that is being tested for quality control in these features.

Figure 2:
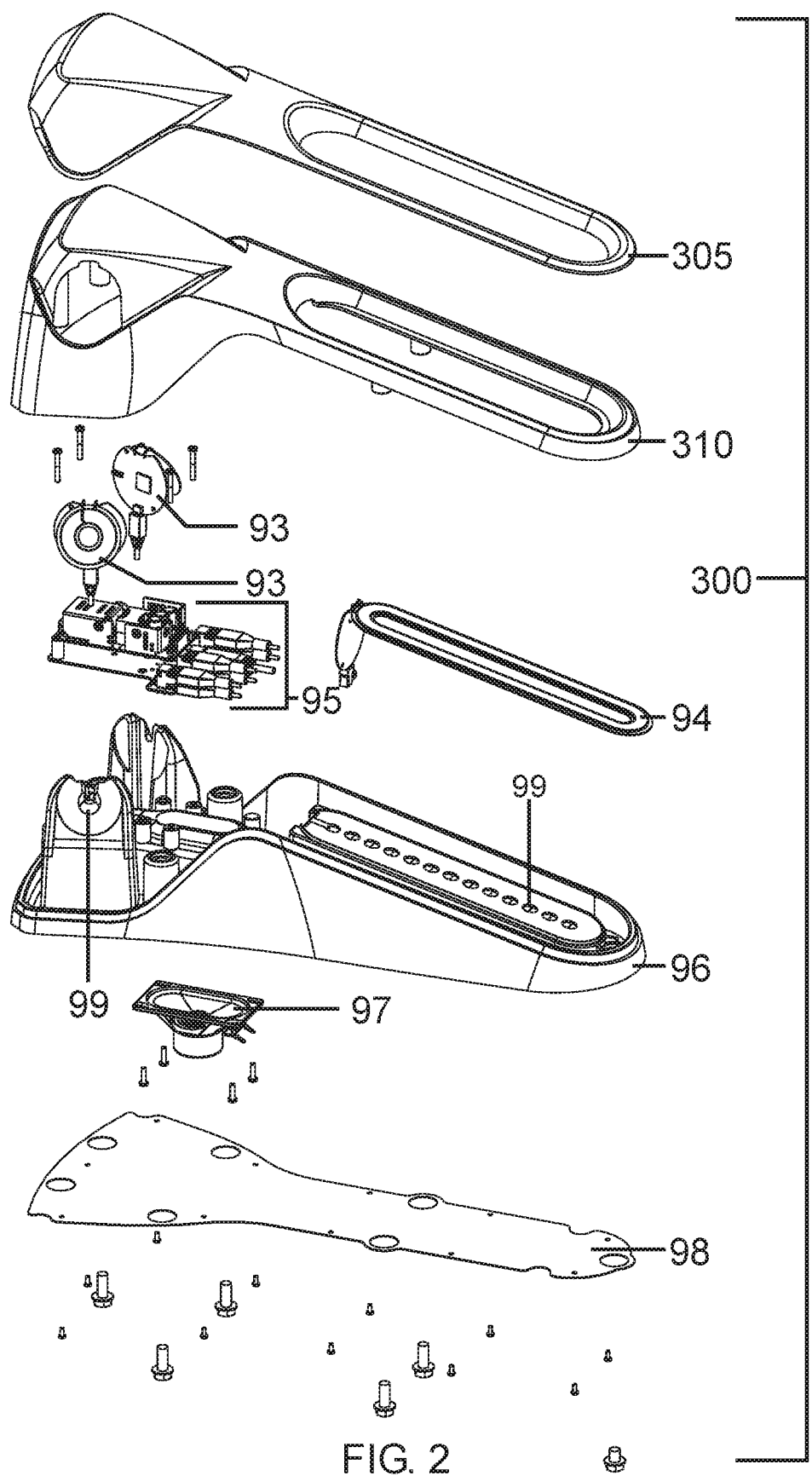
FIG. 2 depicts a base in exploded view.

FIG. 2 details a base 300 that provides for storage, charging, and calibration for the array 5. The base 300 comprises a base enclosure top 310, a base enclosure bottom 96, and a bottom closure plate 98. A decorative elastomeric TPE over-mold 305 can be provided to protect the base 300 and the array 5. The transmit wireless charging coils 93, 94 are arranged to power the optional respective wireless charging coils of the sensor pods 1. Also arranged in the base 300 is a calibration speaker 97. The electronic module 95 powers optional transmit wireless charging coils 93, 94, when utilized with an array having a corresponding charging feature. In other embodiments, a base can directly charge several batteries or a single battery with a mechanical connection, as depicted in FIG. 5, 131, as is known to a person of ordinary skill in the art. In several embodiments, the electronics module generates a calibration and verification signal to be reproduced by the calibration speaker 97. The base enclosure bottom 96 has one or more sound holes 99 arranged therein. The sound may resonate thru 305, eliminating a hole thru the enclosure, preventing the intrusion of cleaning liquids, dust, dirt, hair, etc. into the enclosure. The base can be secured together with fasteners, as depicted, with adhesives, plastic welding, or other similar fastening mechanisms.

In one embodiment, disposed of within the base 300, and specifically adjacent to the cradle for each of the sensor pods 1, is a respective speaker 97. A computer is coupled to the base 300 for communication via a USB connection, Bluetooth, near field communication, RS-232, or the like. The computer couples to the speaker 97, and when the SDD (Stenosis Detection Device) is activated, a program is executed by the computer system so that it performs a diagnostic and quality control test on each of the sensor pods 1.

The diagnostic and quality control procedure comprises a program that plays a known set of sounds generally corresponding to sounds that will be detected and recorded when measuring sounds on the body of a patient. These sounds include low and high frequency sounds, typically low amplitude. Once the sounds are played, the sensor pods 1 detect the sounds and convert the sound to a digital signal that is plotted and compared to a predetermined plot of the sounds that were played. Alternatively, an analog signal is generated and compared with the predetermined plot. Each of the sensor pods 1 is independently tested to determine if it meets an acceptable standard. In one embodiment, and error message is generated if the sensor pod output is not within 10 percent of the predetermined plot at a given data point. Other standards can be used to determine an error condition exists. A range of 1 to 50 percent at each data point can be used to determine if the sensor pod 1 is not functioning properly. Alternatively, the overall plot can be analyzed, instead of a point-by-point analysis, to determine if a sensor pod 1 is functioning properly. Typically, a sensor should be within 25% of a predetermined frequency.

If any sensor pod is not detecting an appropriate sound, then the system will notify the user of an error. In most instances, the error means that a particular sensor pod has exceeded its useful lifetime and is due for replacement. These devices theoretically have a lifespan of several hundred uses under ideal conditions. However, in a medical office, the continuous placing of the array 5 on to a patient, and detecting and recording real sounds, may result in distortion after even a few uses. Accordingly, the system is able to determine whether the detected sounds are simply drift that is a slight change in the detected sounds, or whether there is an error or fault in one of the sensors. If there is only a slight drift, the system can calibrate each unit so that the measured noises from the system are consistent through use.

If the measured sounds are greater than a tolerance of more than 10%, or more than 25% as defined for the occasion, the system notifies the user through images on a display, lights on the sensor pod, audible messages, or other manner to communicate the error, and identifies which sensor pod is faulty. A user can then quickly replace the faulty sensor pod or the disposable piezo assembly 85, and re-run the quality and calibration control program.

After the sensor pod is replaced and the quality control program is re-run, and the replacement sensor pod is confirmed to be working properly, the system will alert that it is ready for placing on a patient. Each of the sensor pods can be appropriately placed onto the patient.

Figure 3:
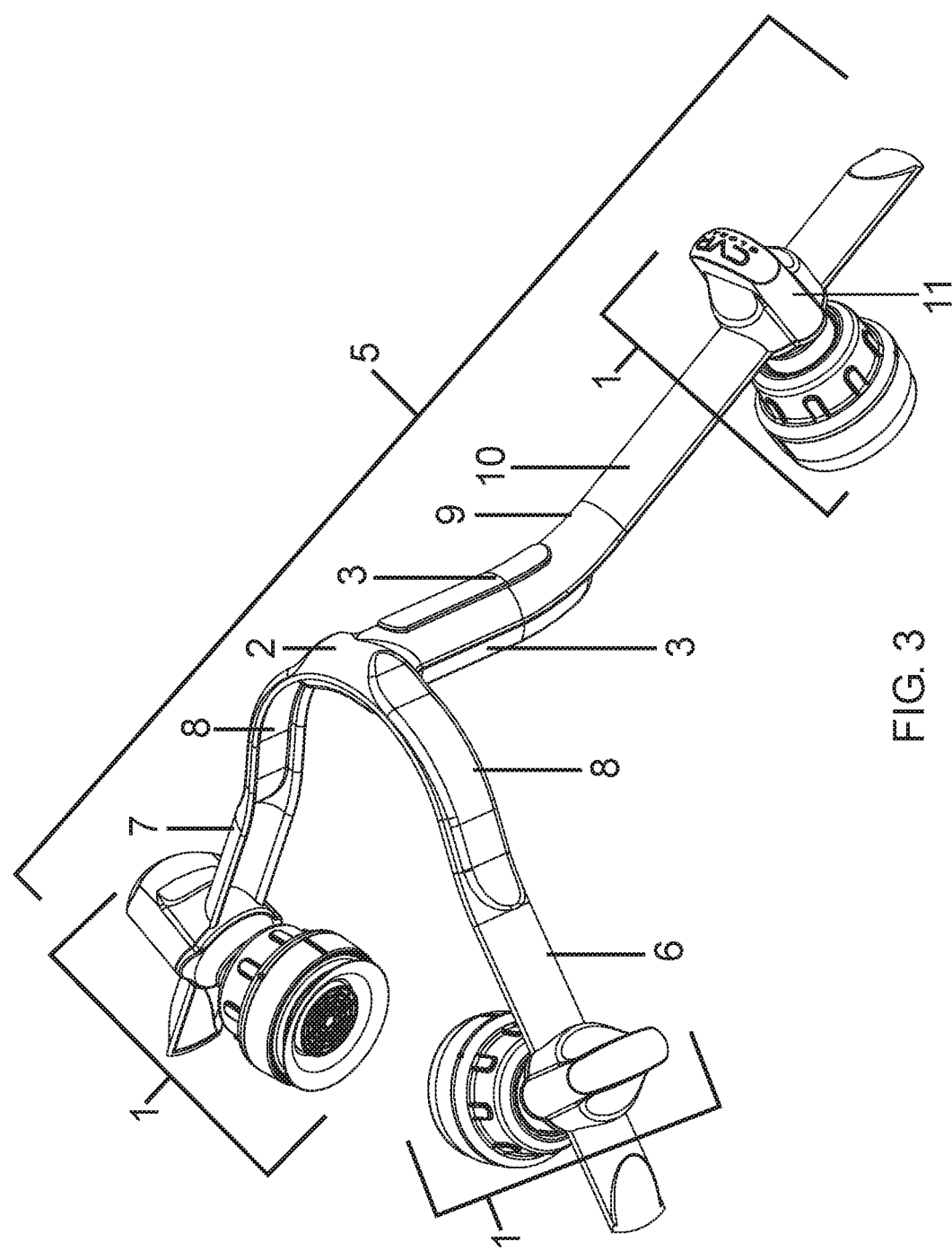
FIG. 3 depicts a detail of an embodiment of an array.

FIG. 3 details an embodiment of a listening device, comprising a yoke 5 having three sensing pods 1. The yoke 5 secures the three sensing pods 1, and by holding the yoke 5 at the neck 3, the sensing pods 1 can be placed against a patient's body, thereby positioning the sensor pods adjacent to the carotid arteries and the sternum. A concern arises, however, where the sensors are not in the correct location on the body, wherein a weak or improper signal is detected by the sensor pods, or when one of the sensing pods is damaged or broken in the process of moving the yoke from the base 300 to the body. This poses a challenge for the operator, as a broken sensing element would provide no signal, and wherein weak signal would not give reliable results. Furthermore, there is obvious concern for a patient, as improper or unreliable results can have significant deleterious effects. As described herein, the device, a system, and methods of use of the device and system, provide for mechanisms to assist with positioning of the device on the body.

Figure 7:
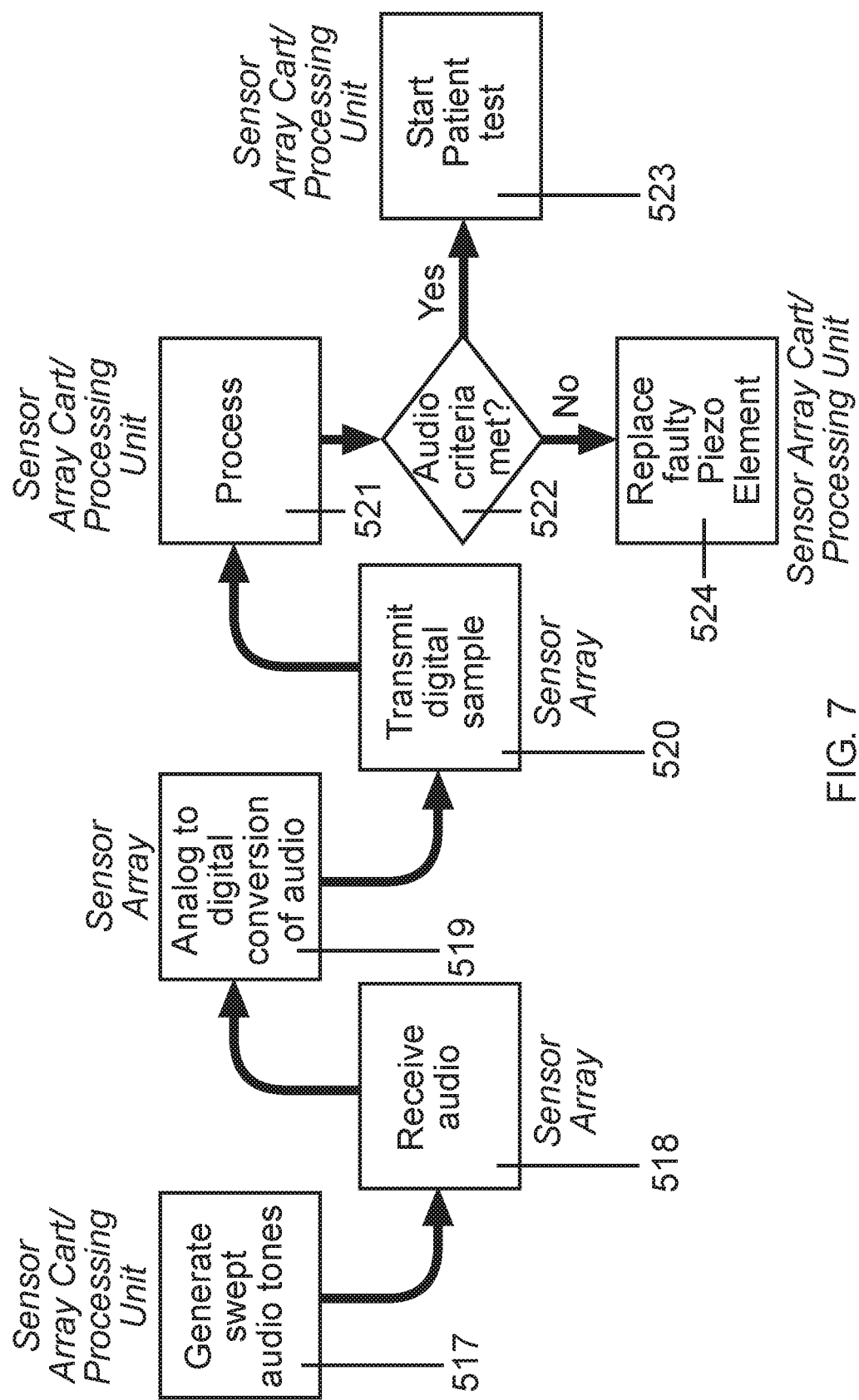
FIG. 7 details a flow-chart of a quality control process.

The diagnostic and quality control procedure is depicted in a flow-chart of FIG. 7. The process includes several steps as defined generally in the flow-chart of steps 517-523. A first step 517 comprises a program that plays a known set of sounds corresponding to sounds that will be detected and recorded when measuring sounds on the body of a patient. The piezos 90 detect the audio 518, which is then converted from analog to digital 519. The digital sample is transmitted 520 to a processing unit for processing 521. A criteria challenge 522 is defined, with the criteria met 523, thus starting a patient test, or not met 524, which requires the replacement of a faulty piezo 90, through replacement of one or more components as defined herein, and restarting the test again at 517 once the piezo is replaced.

When performing the test in step 517, the sounds include low and high frequency sounds, typically at low amplitude corresponding to the range of sounds to be detected by the SDD device. Once the sounds are played, the sensor pods detect the sounds and convert the sound to digital 519. The criteria step 522 compares the digital sounds received to the actual sounds played. For example, a comparison can be made between amplitude and frequency, and overlayed to compare the two samples. Each of the sensor pods is independently determined to meet an acceptable standard, or tolerance for example within 50%, 25%, 10%, 5%, or within about 1% of the sounds based on the determined Hz and, optionally, the amplitude of the detected sounds. Simply comparison software can make these comparisons between the two sounds.

If any sensor pod is not detecting an appropriate sound, then the system will notify the user of an error. In most instances, the error means that the particular sensor pod is due for replacement. While these devices may theoretically have a lifespan of several hundred uses under perfect conditions, the reality of a medical office and placing a device on or adjacent to a patient and detecting and recording real sounds may cause distortion after even a few uses. Accordingly, the system is able to detect and determine whether the sounds detected are simply drift that is a slight change in the detected sounds, or whether there is an error or fault in one of the sensors, thus requiring replacement. If there is only a slight drift, the system can calibrate each unit so that the measured noises from the system consistent through use. An appropriate program on the system can make these changes to the data based on the actual versus detected sounds, through a simple calibration program. Accordingly, the played tones provide for the ability to both detect and calibrate the device before every use.

If the measured sounds differ by more than the acceptable tolerance the system gapes the user through images on the display, lights on the sensor pod, audible messages, or other means for communicating error, and wherein the particular sensor pod that is faulty is identified. A user can then quickly replace the faulty sensor pod or disposable piezo assembly 85, and re-run the quality control program. An exploded view of a sensor pod is depicted in FIG. 5, wherein a portion of the components depicted therein can be appropriately placed in a single replaceable and disposable component for ease of use. This disposable piezo assembly 85 can be secured to the rest of the sensor pod via ordinary connection means such as a swivel mount, bayonet, threaded fastener, snaps, quarter-turn, magnetic, hook and loop, or other known attachment means.

For example, FIG. 5 depicts an outer array half 140, which connects to an inner array half 130. A PCB charger contact 131 provides for an electrical contact between a contact in the base 300 and the array. The wiring harness 132 connects to the PCB processor board in each of the attached sensor pods. So, for example, here there are depicted three sensor pods. However, in embodiments having one, two, or more than three sensor pods, fewer or additional connections would be needed. Furthermore, certain embodiments may utilize a sensor pod having multiple piezo elements. Accordingly, a wire from harness 132 will be necessary for each piezo.

FIG. 5 further depicts an exploded view of a sensor pod, with the entirety of 90 through 125 being a complete sensor pod. By contrast feature 85 depicts a disposable piezo assembly. The disposable piezo assembly 85 comprises a piezo 90, a piezo wiring 91, which connects the piezo 90 to the PCB contact board 105. A piezo cap 100 is surrounded on each side by a pressure sensitive adhesive 92, this pressure sensitive adhesive 92 secures the piezo 90 to the piezo cap 100 and to the PCB contact board 105, on the other side with the second pressure sensitive adhesive 92. These components, can be normally configured in a disposable arrangement, wherein the quarter locking feature 101 can be used to screw on and off the disposable 85 by connection to the quarter turn locking pin 116. The quarter turn feature can be exchanged for other locking or attaching features, such as magnetic attachment, compressions/friction, one or more threaded fasteners, and the like. Known attachment means are known to a person of ordinary skill in the art.

When the disposable piezo assembly 85 is attached, it contacts the PCB Processor board 110, which assembles into a pocket in 115, and is captured by 85. In this manner, when a quality control test is performed, and a sensor is identified as faulty, the attachment means can be withdrawn and the disposable piezo assembly 85 can be removed and a new disposable piezo assembly 85 attached and the test re-run.

In certain embodiments, it is advantageous to have the entire sensor pod replaced, not just the top disposable component. For example, the PCB board 110 may in some instances wear or be damaged. Alternatively, the diaphragm bellows membrane 120 may need replacement, or simply replacement is warranted because of contamination concerns. Accordingly, the entire piezo assembly can be replaced, by removing threaded fasteners 133 or by removing locking cap 125.

The diaphragm bellows membrane 120 locks with certain features, to ensure that it can freely flex and compress to allow for the fit of the piezo against the body. The diaphragm bellows membrane 120 fits feature 121 into a locking groove 117, which traps locking feature 121 between locking cap 125 and the PCB housing 115. Locking feature 122 secures the diaphragm bellows membrane 120 between the inner array halve 130 and the outer array halve 140. This creates a flexible "drum head".

For each use of the piezo, a sensor pad 18 is also utilized for sanitary conditions and to ensure a quality sound contact the piezo 90. The sensor pod 1 of FIG. 3 can be replaced by sliding off the track or removing the track base 11, and replacement by sliding on a new pod, or attaching the new pod over the track.

After either replacement of the disposable component 85 or replacement of the entire sensor pod, the quality control program is re-run and the replacement sensor pod is confirmed to be working properly, the system will alert that e on a patient. Each of the sensor pods can be appropriately placed onto the patient, as depicted in FIG. 10.

Figure 10:
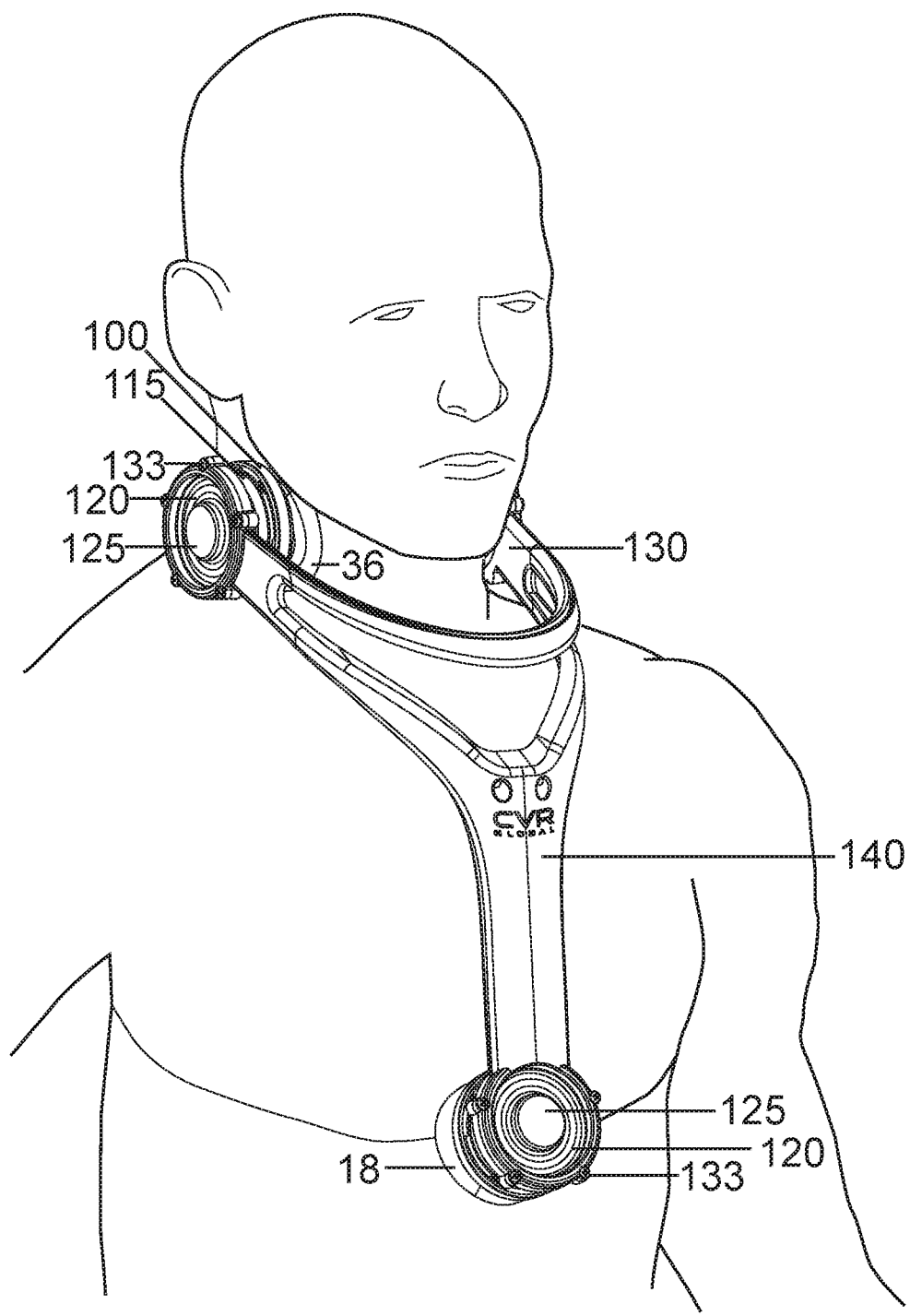
FIG. 10 details an array on a patient.

As depicted in FIG. 10, when the carotid artery is tested, at least one sensor pod is placed adjacent to either the left or right carotid artery. Optionally, a sensor can be placed adjacent to the heart. The sensor pads 18 are placed on the skin of the patient at the carotids. In certain embodiments, the heart sensor, if utilized, can be placed over the clothes of a patient, as it is detecting heart rate, which is sufficiently loud to not need to be directly on the skin. However, for more precise applications, a skin to skin application is needed. Indeed, in certain embodiments, a sensor array comprises only one or only two sensor pods, and no pod is placed adjacent to the heart.

As with the quality control procedure on the base unit, once the sensor pods are placed on the patient, the operator can engage the device to begin detection and recording on the patient. Because the sounds that are being detected and recorded are known within a certain range of sounds, that is, the sounds are generally known to a certain frequency and amplitude, and a further quality control test is performed for a duration of between 1 and 30 seconds. This test provides a quality control diagnostic to ensure that the sensor pods are detecting proper sounds from the patient, and thus confirms two pieces of information: first the proper placement of the sensor pods on the patient; and second that the sensor has not failed in the time between initial quality control tests and placement on the patient.

Since there are at least two and likely three sensor pods, each pod communicates with the computer identifying the detected sounds, which can be recorded by the system and compared in real time to a predicted sound. Accordingly, the sensor pod at the heart will predict a certain sound and the sensor pod(s) at the carotid arteries another sound. If one or more sensors does not detect the predicted sounds, signal will engage to identify the sensor that is not properly detecting the predicted sound. This signal will alert the operator that the sensor pod needs to be adjusted to a different position to properly detect the sounds for the particular test.

Figure 11:
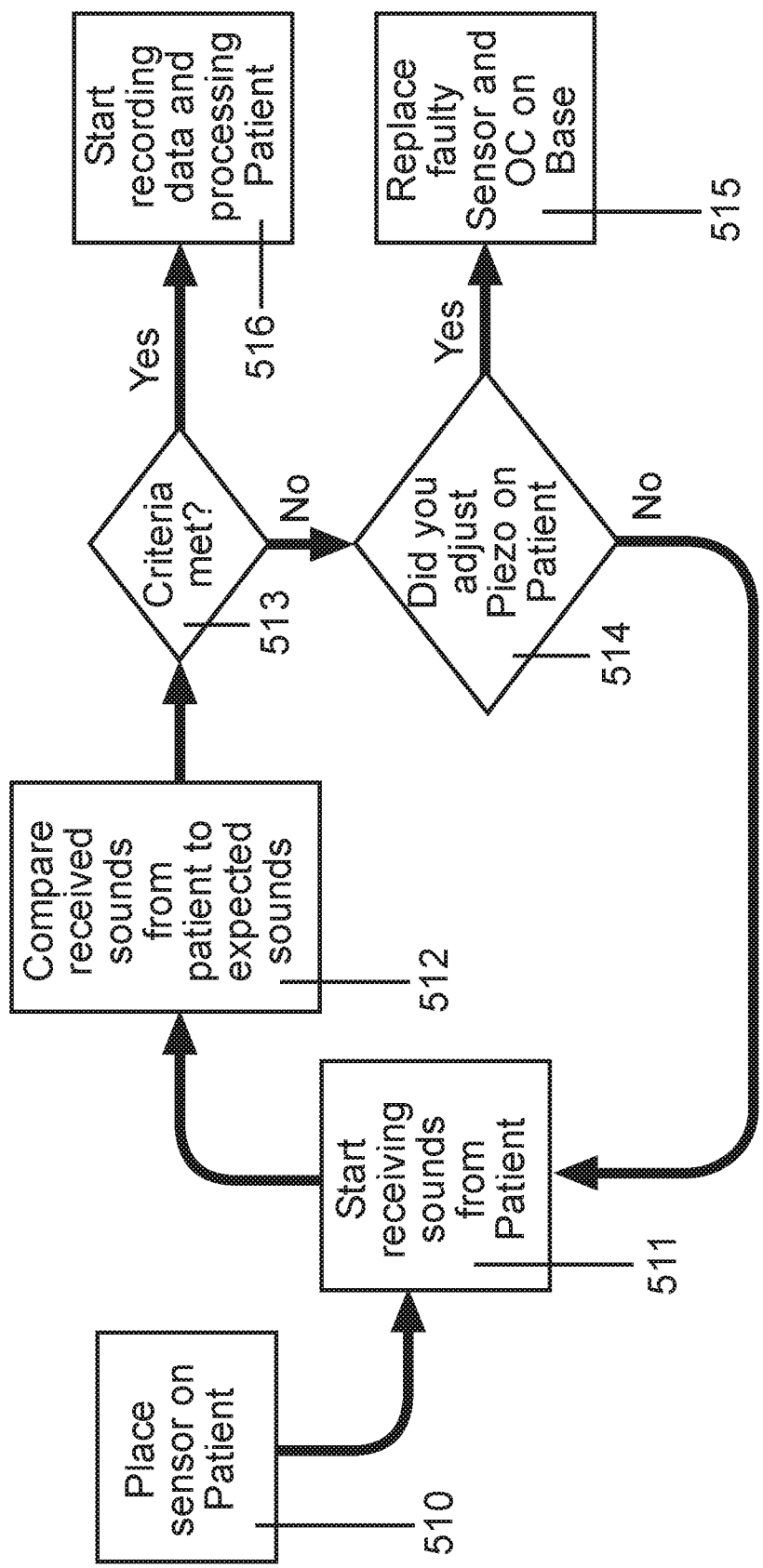
FIG. 11 details a flow-chart of an active quality control procedure.

FIG. 11 provides a representative flow chart of an embodiment of this active quality control process. First, the sensor is placed on the patient 510. The piezos then start receiving sounds from the patient 511. The received sounds are then compared to expected sounds from the patient 512. The comparison identifies an expected frequency at each piezo. For example, we expect to hear the heart beat at about 1 Hz. Accordingly, if this sound is received by the piezos, within 25%, 10%, 5%, or 1% of the expected frequency, then we know that the devices are properly positioned over the carotid arteries. Alternatively, we can look for a frequency between 60 and 260 Hz, which corresponds to the large ring vortices at the carotid artery. This corresponds to the expected stenosisat the carotid artery. Intensity is patient relative. Accordingly, when intensity is utilized as a parameter, an expected value may be assumed, but the system can simply identify relative intensity that is by re-positioning a sensor, the intensity may be increased or decreased from the prior position, with an increase in intensity being an improved position. Accordingly, an indicator on a display, volume of sound being played through the speaker, rate of flashing light on the sensor, sensor array, or the base, or a set of indicator lights, with re lights showing greater intensity and fewer lights showing lower intensity. Those of skill in the art will recognize there are numerous ways to indicate a change of intensity.

If the criteria is met, 513, then we proceed to start recording the data and processing the patient 516. However, if the criteria is not met, we need to first adjust the piezo on the patient 514. Adjustments can be just a few centimeters, or more as necessary, in order to get the piezo closer to the artery of interest. After adjustment the device again receives sounds from the patient 511 and compares the sounds to the expected sounds 512 to determine if the criteria is met.

In certain instances, after movement and adjustment of the device, the piezo is still not finding the proper sounds. This can be due to continued improper placement or failure. Accordingly, it is best to replace the piezo 515 and start another quality control procedure as outlined above on the base.

The embodiments of the system utilize variations of quality control programs for initial setup testing of the sensor pods and then for quality control testing of the proper position on the patient. A variety of alarms, indicators, or signals can be utilized in each of the quality control programs to ensure that the issue is detected and corrected.

Figure 8:
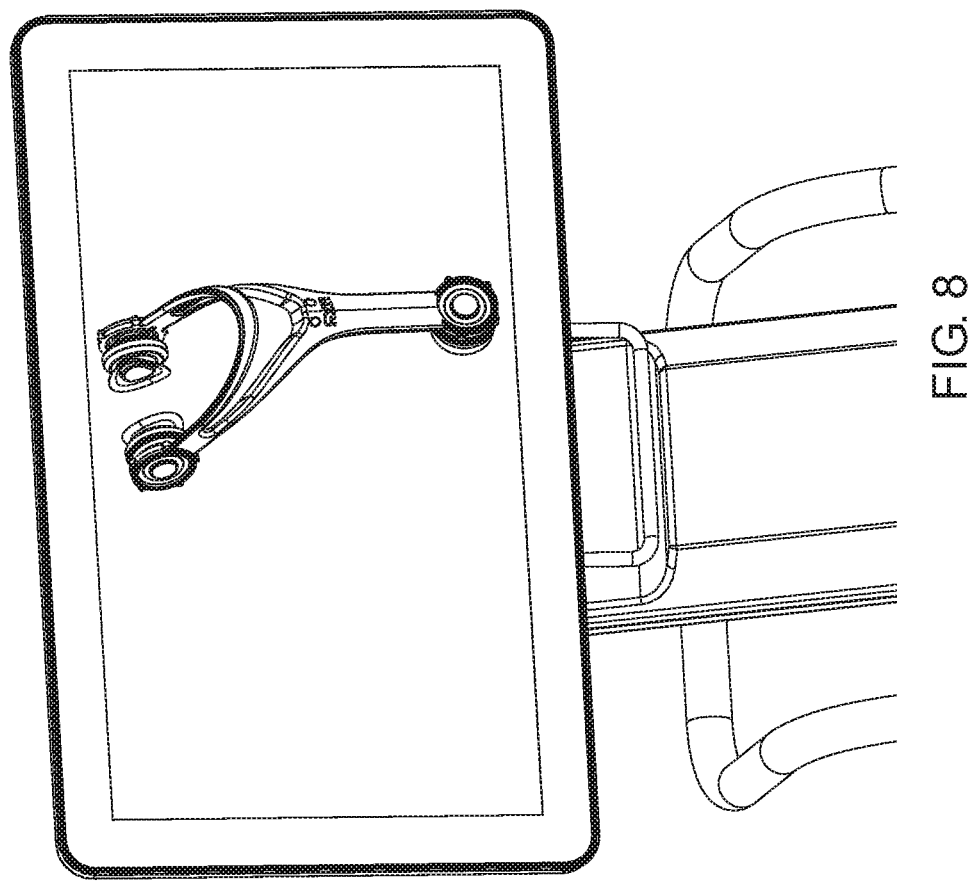
FIG. 8 details a sample GUI.

For the initial quality control program, when the sensor pods are still in the base unit cradle, it is appropriate to indicate a fault with a computer Graphical User Interface (GUI) as depicted in FIG. 8. An image of the specific array and number of sensor pods is indicated on a screen. The system can recognize the number of sensors based on data received and will indicate proper function or improper function of each. For example, the GUI may indicate with a green color at each sensor that it is functioning properly, or a red light when improperly functioning and requiring replacement. Alternatively, an arrow or words may indicate replacement or proper function for each sensor. Instructions to replace a sensor will be indicated on the screen with a step-by-step directions, based on the particular type of connection mechanism. After replacement, the quality control program can be re-run to confirm proper function.

Figure 6:
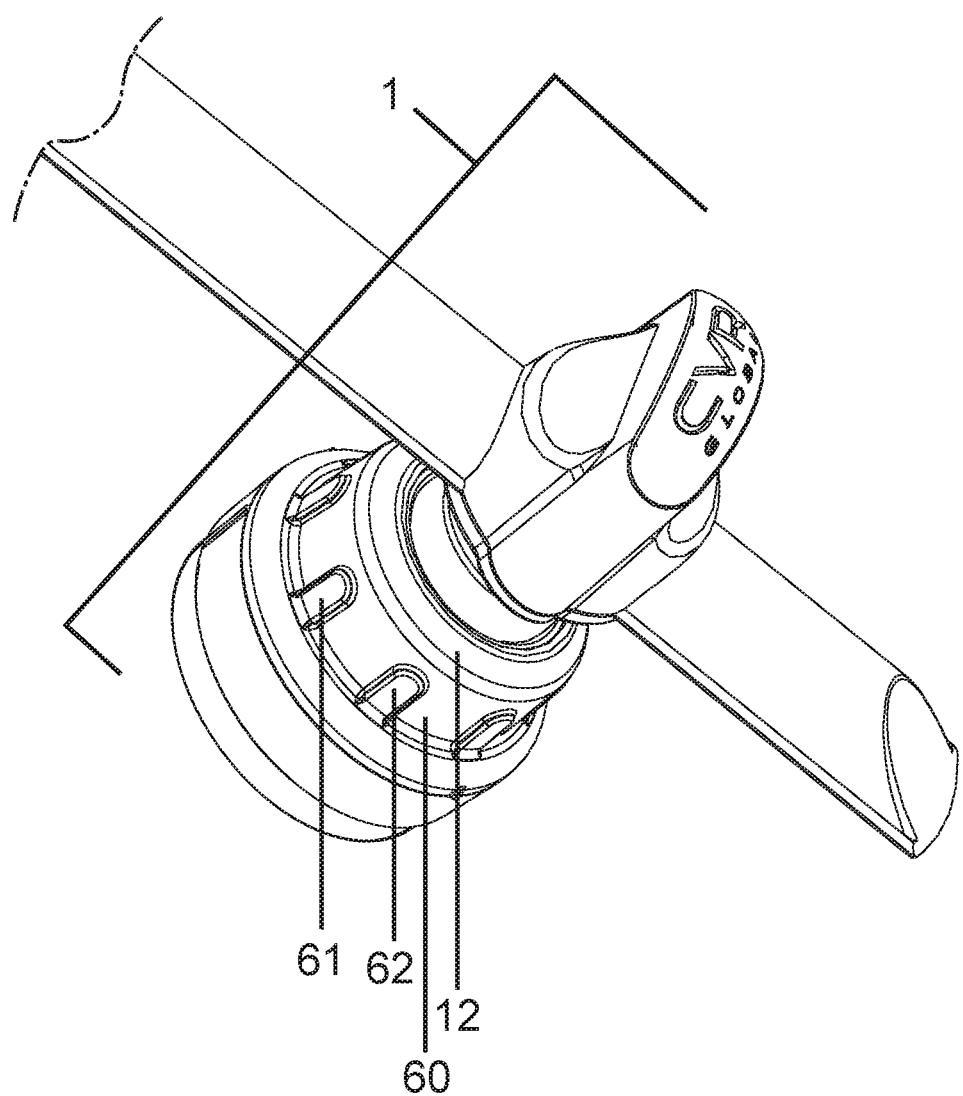
FIG. 6 depicts an example of a sensor pod having attached indicators.

In other embodiments, a colored light system, such as a green or red light based on green being good, and red signaling an error with the sensor pod can be directly placed on the sensor pods (see FIG. 6). Indeed, FIG. 6 depicts an first indicator light 61 and a second indicator light 62 illuminating through a clear, TPE, overmold material 60. These can be illuminated based on the pass or fail of a particular process. A third or additional lights are depicted, but not labelled, and can be further utilized as described herein.

Figure 9:
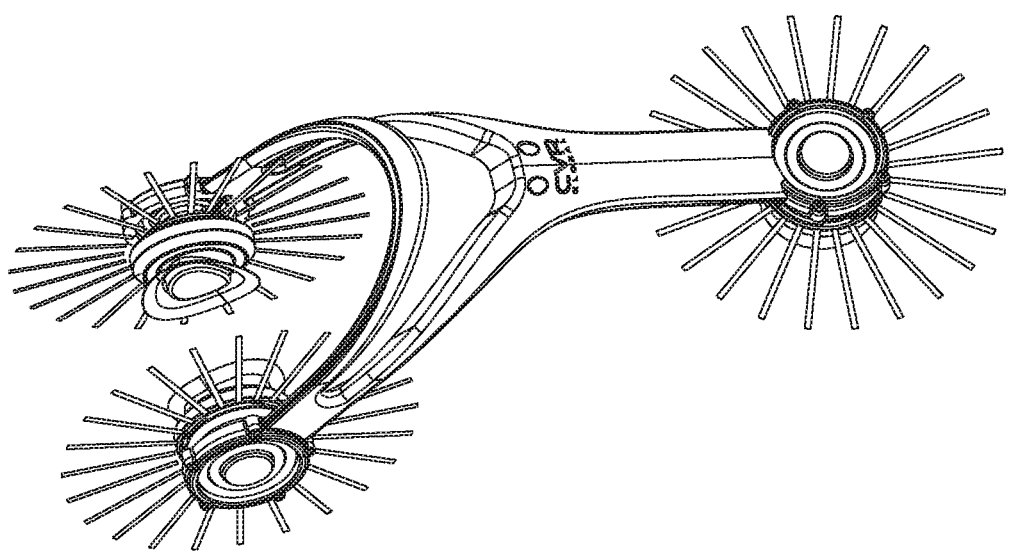
FIG. 9 details an example of light indicators indicating after a test.

FIG. 9 depicts a plurality of lights will indicate based on the self-diagnostic phase of the test. Color changing LED lights, or simply alternating LED lights, or an equivalent, can be used to provide easy indication with different colored lights, shown through clear or translucent plastic housing. These lights can be placed on the base unit itself. In other embodiments, or in addition to these lighting systems, an audible alarm may signal from the SDD device to warm of an error. Furthermore, the display unit may further provide for a display indicating which of the sensor pods needs to be replaced.

The lights of FIG. 6 and FIG. 9 can also be used during the active diagnostic phase. For example a set of three lights can be used, green indicating proper sounds received and proper placement and red for improper placement or failure, i.e. not meeting one or both criteria. However, a yellow light may be further included for several reasons. First, the yellow light may hold steady or flash to indicate that the self-diagnostic or active diagnostic phase is being performed. The yellow light may stay illuminated, or joined with a green or with a red, if, for example one of the criteria are not met. This would indicate that the sensor is functioning but that it is improperly placed. For example, the intensity is not sufficient, or the frequency improper, would suggest that the device is not in the proper locating for high quality data. The device can be adjusted on the patient and the active diagnostic phase continues until either a green light is indicated for all sensors or a single red light is indicated on one sensor.

In certain embodiments, a button on the device or on the base is pressed to perform the active diagnostic phase. However, in preferred embodiments, once the self-diagnostic test is complete, the active diagnostic phase immediately starts. The active diagnostic phase will continue, until either all sensors indicate green or one indicates red. Typically, this will last up to 30 seconds, at which time a red light will indicate to re-start the test, or to replace a sensor.

If one sensor remains yellow or yellow with green/red, during the active diagnostic step, the lights, visual, and or audible alarms can further assist in positioning the device properly on a patient. For example, the light remaining yellow will turn to yellow and green, if the signal is better, or from yellow to yellow and red, if the signal is worse. Accordingly, the sensor can be moved in a proper direction towards the yellow/green until just a green light is indicated. Furthermore the GUI can be utilized in the same manner, with an indicator on the screen suggesting the direction to move the sensor. Ultimately, if a sensor pod does not detect the proper sounds from the patient, then one or more alarms will register and the operator will know that one or more sensor pods need to be replaced on the patient. In certain embodiments, the visual screen, a visual identifier will flash to aid the operator in placing the sensor pod in the proper location.

In further embodiments, where a sensor pod is identifying an improper sound or not detecting a sound, a visual alarm may be generated, such as a red light, which indicates improper position or a sensor failure. The SDD can detect and compare the sounds in real-time, so the operator can then slowly move the sensor pod to a different location and wait a few seconds to see if the light turns from red to green, indicating a proper position. The operator can continue to move the sensor pod on the patient until it is indicated on either the sensor pod, on the array, or on the SDD device display that the position is correct.

If the operator is unable to determine a proper location on the patient after 30 seconds, the SDD will alarm with a visual or audio signal to perform a base unit quality control procedure again to ensure that the sensor pods are all functioning correctly, or to simply replace the sensor that indicated failure. After replacement or if the sensor pods are determined to be functioning correctly, the operator can again restart the process of placing the sensor pods on the patient.

Accordingly, a preferred embodiment for determining proper placement of sensor pods on a patient comprises a stenosis detection system comprising a base unit having a cradle, at least two sensor pods, a display and at least one alarm mechanism; wherein while the sensor pods are engaged in the base unit cradle a self-diagnostic quality control procedure is performed to confirm that the sensor pods are properly functioning. After confirmation of the proper function of each of the sensor pods, the devices can be placed onto a patient wherein an active quality control procedure is performed. The active quality control program is run for between 1 and 30 seconds wherein each sensor pod is communicating with the compute of the detection system in real-time to ensure that each of the sensor pods is measuring the appropriate sounds. Wherein the system provides for an audio or visual notification that the active quality control program is met, or wherein the system identifies one or more sensor pods that are improperly placed. Wherein the system then provides an alarm to any sensor pod that is not properly placed. Wherein a visual or audio mechanism is provided to provide real-time feedback as to the proper position for each sensor pod, and wherein one example provides for a red light for improper position and green light for a proper position. Certain embodiments utilize a yellow light to indicate that one or more of the self-diagnostic test or active diagnostic test are proceeding.

Other audio or visual alarms or mechanism may be further included in the system so as to aid in the placement of the sensor pods on a patient.

In preferred embodiments, the active quality control step on the patient provides for immediate real-time feedback to the correct placement of each sensor pod to ensure fast and reliable positioning of the sensor pods, and also to confirm fast, precise, and accurate detection and determination of stenosis on the patient.

The method comprises: Performing a first base unit quality control test; confirming that each of the sensor pods is properly functioning; placing sensor pods on a patient; performing a second quality control test, wherein the sensor pods detect sound in real-time and compare said sound to a predicted sound; and indicating with an alarm whether the sensor pod is properly placed on the patient by comparing the detected sound in real-time to a predicted sound based on historical data.

In a preferred embodiment the system uses a computer to run software to implement the features as described in the embodiments herein. Accordingly, the computer is connected to the array and/or to the sensor pods via a connection means either wired or wireless, as is known to one of ordinary skill in the art. The software comprises the various quality control procedures, as well as appropriate code to provide alarms and to notify of the need for replacement or modification. Further features include the ability to calibrate the system in view of a quality control test.

Therefore, preferred embodiments of the disclosure comprise a method of confirming the proper position of a medical device upon a patient comprising: performing a first quality control procedure to ensure functioning of the sensor pods, comprising playing a predetermined set of sounds and comparing the predetermined sounds to the detected sounds; performing a second quality control procedure while detecting sounds from a patient wherein the test compares the detected sounds to sounds that are ordinarily present in detection of the particular artery or vessel of interest; and triggering an alarm wherein the detected sound does not meet the predicted sound, or triggering an approval if the detected sound confirms with the predicted sound.

What is claimed is:

1. A method for performing a quality control process on a sensor comprising performing the following steps in order:
   b. placing a sensor adjacent to a skin surface of a patient, said sensor comprising a piezoelectric element for detecting sound waves generated under said skin surface;
   c. detecting said sound waves with said sensor;
   d. comparing said detected sound waves to a predetermined sound fingerprint corresponding to the area of skin surface being tested;
   e. determining whether said piezoelectric element is functioning wherein proper functioning is determined when said detected sound waves are within a predetermined tolerance of said sound fingerprint;
   f. adjusting the sensor's position if the detected sound waves are outside of a predetermined tolerance and reperforming the test at a new position; and
   g. wherein said detected sound waves are outside of the predetermined tolerance at the new position, replacing said piezoelectric element if said detected waves are outside of said predetermined tolerance; and
   h. proceeding to take a data sample from said patient upon confirmation that the piezoelectric element is detecting said sound waves within said predetermined tolerance.

2. The method of claim 1, wherein said predetermined tolerance is 25%.

3. The method of claim 1, wherein the step of replacing said piezoelectric element comprises replacing said sensor.

4. The method of claim 1, wherein said sensor is a part of a listening device, said listening device comprising at least one sensor comprising a sensing element and a base, said base comprising at least one speaker and a processing unit configured to play a pre-determined set of tones through said speaker; and the method further comprises the steps before placing said sensor adjacent a skin surface:
   a1. playing a pre-determined set of tones through said speaker;
   a2. detecting said pre-determined tones in said at least one sensing element;
   a3. comparing the pre-determined tones to the detected tones; and
   a4. providing an indicator that the pre-determined tones are within a pre-determined tolerance of the detected tones or not by indicating an approval if the detected tones are within said tolerance and indicating a rejection if the detected tones are outside of said tolerance.

5. The method of claim 4, wherein the skin surface is adjacent to the carotid artery.

6. The method of claim 5, wherein the notification is selected from a tone, light, visual, or audio notification.

7. The method of claim 5, wherein the notification is provided on the sensor pod.

8. The method of claim 5, wherein a further step comprises replacing said sensing element if a notification is provided, and restarting the quality control procedure.

9. The method of claim 4, wherein the indicator is selected from a tone, light, visual, or audio indication.

10. The method of claim 4, wherein the indicator is provided on the base.

11. The method of claim 4, wherein a further step comprises replacing said sensing element if a rejection is provided, and restarting the quality control procedure.

12. The method of claim 1, wherein said step of placing said sensor adjacent a skin surface of a patient comprises placing a sensor pad having a first side and a second side, with said first side in contact with said sensor and said second side in contact with a skin surface.

\* \* \* \* \*